(12) United States Patent
Sato et al.

(10) Patent No.: US 7,067,491 B2
(45) Date of Patent: Jun. 27, 2006

(54) HETEROCYCLIC COMPOUNDS HAVING ELASTASE-INHIBITING ACTIVITY AND INTERMEDIATES THEREOF

(75) Inventors: Fuminori Sato, Kobe (JP); Takashi Deguchi, Kobe (JP); Ryotaro Shiratake, Osaka (JP); Hiroshi Okazaki, Toyonaka (JP); Akemi Kuromiya, Daito (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 10/502,768

(22) PCT Filed: Feb. 5, 2003

(86) PCT No.: PCT/JP03/01153
§ 371 (c)(1),
(2), (4) Date: Jul. 28, 2004

(87) PCT Pub. No.: WO03/066671
PCT Pub. Date: Aug. 14, 2003

(65) Prior Publication Data
US 2005/0085424 A1    Apr. 21, 2005

(30) Foreign Application Priority Data
Feb. 5, 2002    (JP) .............................. 2002-027634

(51) Int. Cl.
*A61K 38/00*    (2006.01)
(52) U.S. Cl. ...................................................... 514/19
(58) Field of Classification Search .................. None
See application file for complete search history.

(56) References Cited
FOREIGN PATENT DOCUMENTS

| | | |
|---|---|---|
| EP | 189305 | 7/1986 |
| EP | 1157998 | 11/2001 |
| WO | WO 03066671 * | 8/2003 |

OTHER PUBLICATIONS

Joseph P. Burkhart,; Preparation of alpha keto ester enol acetate as potential prodrugs of human neutrophil elastase inhibitors. Bioorganic & medicinal chemistry letters,; Jan. 6, 1998, pp. 63-64. (abstract only).*

Fuminori Sato, et al.; Design and synthesis of peptide -based carboxylic acid-containing transition-state inhibitors of human neutrophil elastase, Bioorganic & medicinal., Feb. 25, 2002, pp. 551-555. (abstract only).*

P.D. Edwards et al., "Discovery and Biological Activity of Orally Active Peptidyl Trifluoromethyl Ketone Inhibitors of Human Nautrophil Elastase", J. Med. Chem., vol. 40, No. 12, 1997, pp. 1876-1885.

* cited by examiner

*Primary Examiner*—Bruce R. Campell
*Assistant Examiner*—Shyam Shirali
(74) *Attorney, Agent, or Firm*—Wenderoth, Lind & Ponack, L.L.P.

(57) ABSTRACT

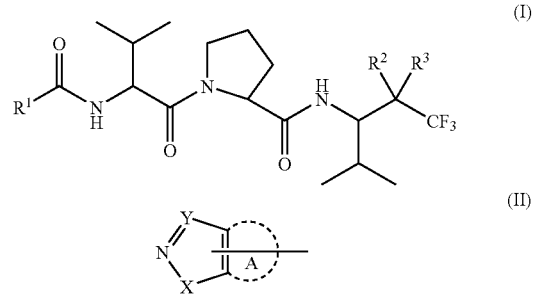

Heterocyclic compounds represented by the general formula (I) and having elastase inhibiting activity; and intermediates for the synthesis thereof: (I) wherein $R^1$ is a heterocyclic group represented by the general formula (II): (II) [wherein A represents the presence or absence of a benzene ring; X is oxygen, sulfur or NH; and Y is nitrogen or CH], and the heterocyclic group may be substituted with one to three substituents which may be the same or different and are selected from the group consisting of lower alkyl, lower alkoxy, and phenyl which may be substituted with optionally halogenated lower alkyl, lower alkoxy or halogeno; and $R^2$ and $R^3$ are each hydrogen or hydroxyl, or $R^2$ and $R^3$ may be united to form an oxo group, with the proviso that both are not hydrogen.

12 Claims, No Drawings

SEQUENCE LISTING

<160> NUMBER OF SEQ ID NOS: 1

<210> SEQ ID NO 1
<211> LENGTH: 4

```
<212> TYPE: PRT
<213> ORGANISM: Artificial Sequence
<220> FEATURE:
<223> OTHER INFORMATION: Description of Artificial Sequence: substrate
      of elastase, MeO-Suc-peptide-pNA

<400> SEQUENCE: 1

Ala Ala Pro Val
 1
```

HETEROCYCLIC COMPOUNDS HAVING ELASTASE-INHIBITING ACTIVITY AND INTERMEDIATES THEREOF

This application is a U.S. national stage of International Application No. PCT/JP03/01153 filed Feb. 5, 2003.

TECHNICAL FIELD

The present invention relates to a medicament, especially a novel heterocyclic compound having elastase inhibitory activity, its intermediate and an elastase inhibitory agent containing the said novel compound as an active ingredient.

BACKGROUND ART

Elastase is a general term for proteases which degrade elastin constituting the connective tissue. Neutrophil elastase, pancreas elastase, metallo elastase, etc., are known as elastase. The former two are structurally similar proteases and have the similar specificity against the substrate.

Neutrophil elastase is a serine protease which is contained in granules of neutrophils. A large amount of neutrophil elastase is released from accumulated neutrophils in the tissue in case of suffering from an infectious disease or an inflammatory disease. The neutrophil elastase degrades proteins constituting the interstitium in various tissues of lung, cartilage, vessel wall, etc., such as elastin, collagen, proteoglycan, fibronectin and so on. It is also known that neutrophil elastase participates in degradation of other various proteins and injury of cells. Usually the activity of neutrophil elastase is controlled not to be in excess by an endogenous protease inhibitor such as $\alpha_1$-protease inhibitor, etc. However, it is considered that in the tissue where drastic inflammation occurs, as the amount of neutrophil elastase secreted from neutrophils increases and the endogenous protease inhibitor is inactivated by reactive oxygen spieces produced in that area, neutrophil elastase acts excessively and therefore, the tissue is injured. So it has been desired to have a medicament having neutrophil elastase inhibitory activity.

The diseases which neutrophil elastase participates in include chronic obstructive pulmonary disease (including pulmonary emphysema and chronic bronchitis), chronic and acute interstitial pneumonia, idiopathic interstitial pneumonia (IIP), diffuse panbronchiolitis, cystic lung fibrosis, acute lung injury (ALI)/acute respiratory distress syndrome (ARDS), bronchiectasis, asthma, pancreatitis, nephritis, hepatitis (hepatic failure), chronic rheumatoid arthritis, arthrosclerosis, osteroarthritis, psoriasis, periodontal disease, atherosclerosis, organ transplant rejection, tissue injury caused by ischemia/reperfusion, shock, septicemia, blood coagulopathy including disseminated intravascular coagulation (DIC) and deep vein-thrombosis, conjunctivitis, keratitis, corneal ulcer, Crohn's disease, systemic lupus erythematosus, etc.

Furthermore, pancreas elastase is originally an exocrine digestive enzyme, but it is considered that pancreas elastase participates in injury of the pancreas tissue due to autodigestion in case of pancreatitis.

Thus, although neutrophil elastase (and pancreas elastase in pancreatitis) is considered to participate in various chronic or acute diseases, there are a few compounds showing practical elastase inhibitory activity by oral administration and applicable to its chronic disease. Therefore, it is considered that an elastase inhibitory agent which is orally active is effective as a treating or prophylactic agent for these diseases.

Under such expectation, various elastase inhibitors have been reported. For example, in European patent publication A 189305, many kinds of compounds having elastase inhibitory activity are disclosed. In claim 1 of the said patent publication, a compound represented by a following general formula (A-1) (corresponding to the formula Ib of the said publication);

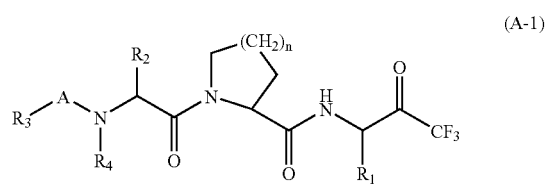

wherein in the above formula (A-1), $R_1$ is alkyl having 1 to 5 carbon atoms (See page 240 of the said publication), $R_2$ is a group selected from alkyl having 1 to 10 carbon atoms, etc. (See page 241 of the said publication), $R_4$ is hydrogen, etc., (See page 259 of the said publication), A is —CO—, etc., (See page 259 of the said publication), and n is 1, etc., (See page 259 of the said publication) is described.

When the definitions of the above $R_1$, $R_2$, $R_4$, A and n are applied to the above formula (A-1), the following formula can be written:

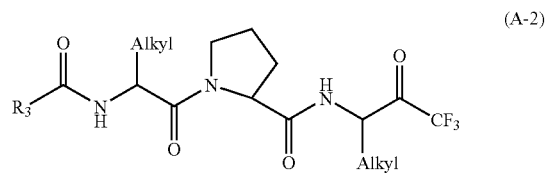

By the way, $R_3$ in the formula (A-2) is defined at pages 245–259 of the said publication. Although this definition is not surely clear, the definition of $R_3$ in the item (VIII) described at page 258 of the said publication is relatively concerned to the compounds of the present invention mentioned below. Namely, $R_3$ in the item (VIII) is defined as:

"an aromatic heterocyclic group containing (a) from 1 to 15 carbons and from 1 to 4 heteroatoms each of which is selected independently from the group consisting of sulfur, nitrogen and oxygen, and (b) from 1 to 3 five or six-membered rings at least one of which is aromatic, and optionally, wherein up to 3 carbons of the aromatic ring(s) may be substituted at any carbon atom with a member of the group consisting of fluoro . . . , and provided further that any nitrogen may be substituted by an alkyl group containing from 1 to 6 carbons, provided that when A is OCO or NHCO then A must be bonded to a carbon of the aromatic heterocycle".

However, in the proviso (3) at page 260 of the said publication, it is defined that no heteroatom may be directly bonded to a sulfur, nitrogen or oxygen. Judging from this definition, it is clear that the compounds of the present invention mentioned below are not included therein. Furthermore, no concrete compound wherein $R_3$ in (A-2) corresponds to the above item (VIII) is described in the said publication at all.

In addition, in J. Med. Chem., 1997, 40, 1876–1885, compounds included in the formula (A-2) of the said publication are described and following compounds as a compound relatively similar to the compounds of the present invention are described:

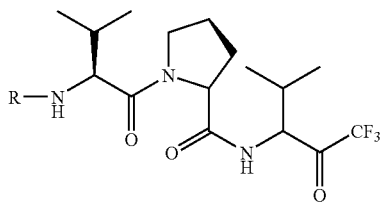

wherein R is 2-pyridylcarbonyl, 3-pyridylcarbonyl, 4-pyridylcarbonyl or 4-imidazolecarbonyl.

Although a compound wherein R is 2-pyridylcarbonyl shows a weak activity in Table 2 (page 1880) of the above article, these compounds are reported to have been inactive in the oral model (page 1879, right column lines 9–10).

DISCLOSURE OF INVENTION

The present invention is to provide a novel compound having excellent elastase inhibitory activity even in oral administration.

The present inventors extensively studied and found that a compound prepared by binding a specific unsaturated heterocyclic group on N-terminal part of a peptidyl trifluoromethyl ketone compound shows excellent elastase inhibitory activity even in oral administration. Thus, the present invention has been completed.

The present invention relates to a heterocyclic compound represented by the following formula (I) and a salt thereof;

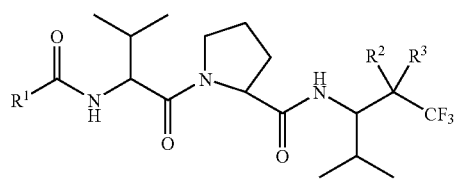

wherein $R^1$ is a heterocyclic group represented by the formula;

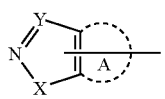

in which A means the presence or absence of benzene ring, X is oxygen atom, sulfur atom or NH, Y is nitrogen atom or CH, and the said heterocyclic group may be substituted by 1 to 3, and the same or different, substituents selected from the group consisting of lower alkyl group; lower alkoxy group; and phenyl group which may be substituted by lower alkyl optionally substituted by a halogen atom, lower alkoxy or a halogen atom; and $R^2$ and $R^3$ are hydrogen atom or hydroxy group, or both may be taken together to form an oxo group, provided that both are not hydrogen atom.

The present invention provides illustratively a heterocyclic compound represented by the following formula (I-a) and a salt thereof;

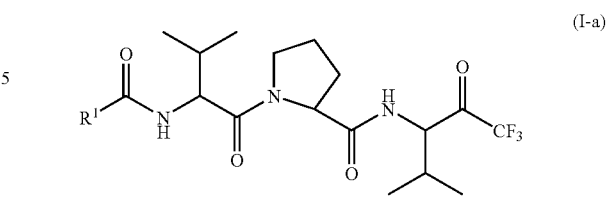

wherein $R^1$ is the same as defined above, and a heterocyclic compound represented by the following formula (I-b) and a salt thereof;

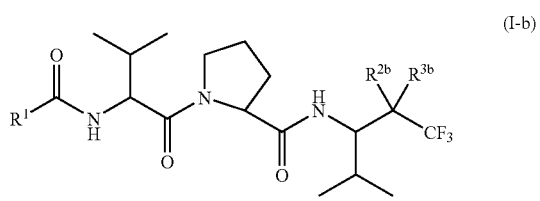

wherein $R^1$ is the same as defined above, $R^{2b}$ and $R^{3b}$ are hydrogen atom or hydroxy group, provided that both are not hydrogen atom.

The present invention also relates to a pharmaceutical composition comprising a heterocyclic compound represented by the above general formula (I-a) or a pharmaceutically acceptable salt thereof, an elastase inhibitory agent comprising as an active ingredient a heterocyclic compound represented by the above general formula (I-a) or a pharmaceutically acceptable salt thereof, and a method for treating a disease caused by increased elastase activity which comprises administering to a patient an effective amount of a heterocyclic compound represented by the above general formula (I-a) or a pharmaceutically acceptable salt thereof.

The compound of the above general formula (I-a) has excellent elastase inhibitory activity even in oral administration. A partial structure represented by the following formula;

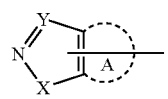

greatly contributes so as to exhibit such excellent property of the compound (I-a) of the present invention. Namely, the said heterocyclic group has to contain a nitrogen atom, and the said nitrogen atom directly binds with at least one heteroatom to form a ring.

Therefore, the primary characteristic of the chemical structure of the compound (I) of the present invention consists in the above mentioned specific partial structure. The secondary characteristic of the chemical structure of the compound (I) of the present invention consists in a combination of the above specific partial structure and the rest of the structure.

BEST MODE FOR CARRYING OUT THE INVENTION

The compound (I) of the present invention is in more detail explained.

In the compounds represented by the above general formula (I), the compound (I-a) wherein $R^2$ and $R^3$ are taken together to form an oxo group, and preferably, a heterocyclic compound represented by the following formula (I-c) and a salt thereof;

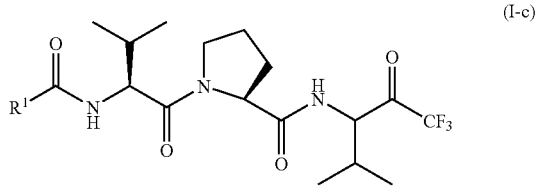

(I-c)

wherein $R^1$ is the same as defined above, have excellent elastase inhibitory activity.

Furthermore, in the compounds represented by the above formula (I-b), the compound wherein $R_2$ and $R_3$ are different from each other and hydrogen atom or hydroxy group, is useful as a direct intermediate for preparation of the above compound (I-a) having elastase inhibitory activity. The compound wherein both of $R^2$ and $R^3$ are hydroxy group corresponds to the compound prepared by adding a water molecule to the compound (I-a), and the compound is dehydrated (by equilibrium reaction) to form the compound (I-a).

Heterocyclic Group:

In the compound of the present invention, the heterocyclic group represented by the following formula;

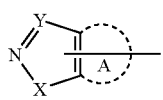

wherein A, X and Y are the same as defined above, includes, for example, isoxazolyl, isothiazolyl, 1,2,3-thiadiazolyl, benzo[d]isoxazolyl, pyrazolyl, benzotriazolyl, benzo[3,4-d]1,2,3-thiadiazolyl, triazolyl, 1H-indazolyl, etc., preferably isoxazolyl, benzo[d]isoxazolyl and pyrazolyl.

Substituents on the Heterocyclic Group:

Substituents optionally binding on the heterocyclic group include lower alkyl group; lower alkoxy group; and phenyl group which may be substituted by lower alkyl optionally substituted by a halogen atom, lower alkoxy or a halogen atom.

The lower alkyl group means straight or branched $C_{1-6}$ alkyl group, preferably $C_{1-4}$ alkyl group. Examples of the lower alkyl group are methyl, ethyl, n-propyl, isopropyl, n-butyl, isobutyl, sec-butyl, tert-butyl, pentyl, isopentyl, neopentyl, hexyl, etc.

The lower alkoxy group means straight or branched $C_{1-6}$ alkoxy group, preferably $C_{1-4}$ alkoxy group. Examples of the lower alkoxy group are methoxy, ethoxy, n-propoxy, isopropoxy, n-butoxy, isobutoxy, sec-butoxy, tert-butoxy, pentyloxy, hexyloxy, etc.

The phenyl group which may be substituted by lower alkyl optionally substituted by a halogen atom, lower alkoxy or a halogen atom means phenyl and phenyl substituted by 1 to 5 the above lower alkyl group, the above lower alkyl substituted by a halogen atom, the above lower alkoxy, or a halogen atom. The halogen atom means fluorine atom, chlorine atom, bromine atom and iodine atom. The lower alkyl substituted by a halogen atom means one wherein at least one (e.g., 1 to 5, preferably 1 to 3) hydrogen atom of the above lower alkyl is substituted by the same or different halogen atom(s) (fluorine atom, chlorine atom, bromine atom, iodine atom). Examples thereof are chloromethyl, difluoromethyl, trichloromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl, 6,6,6-trifluorohexyl, etc.

Following examples of the said phenyl group are illustrated: phenyl, tolyl, xylyl, mesityl, cumenyl, 4-(tert-butyl)phenyl, 4-chlorophenyl, 3-chlorophenyl, 2-chlorophenyl, 2,3-dichlorophenyl, 2,4-dichlorophenyl, 3,4-dichlorophenyl, 2,5-dichlorophenyl, 2,6-dichlorophenyl, 3,5-dichlorophenyl, 2-fluorophenyl, 3-fluorophenyl, 4-fluorophenyl, 2-bromophenyl, 3-bromophenyl, 4-bromophenyl, 2,4-difluorophenyl, 2,3-difluorophenyl, 2,5-difluorophenyl, 3,5-difluorophenyl, 3,4-difluorophenyl, 4-bromo-2-fluorophenyl, 2-methoxyphenyl, 3-methoxyphenyl, 4-methoxyphenyl, 3,4-dimethoxyphenyl, 3-trifluoromethylphenyl, 4-trifluoromethylphenyl, 4-chloro-2-methoxyphenyl, 4-chloro-3-methoxyphenyl, 3-chloro-4-methoxyphenyl, 2-methyl-4-methoxyphenyl, 4-methyl-3-chlorophenyl, 3-methyl-4-chlorophenyl, 3-chloro-2-fluorophenyl, 4-chloro-2-fluorophenyl, 2-chloro-4-fluorophenyl, 2-chloro-6-fluorophenyl, 3-chloro-4-fluorophenyl, 4-chloro-2-fluorophenyl, etc. The position of the substituent(s) is not limited.

The said hetrocyclic group in $R^1$ of the compound of the present invention may have the 1 to 3 substituents above mentioned on the possible position(s) on the ring, and when the number of the substituents are 2 or 3, each substituent is the same or different. The substituent may be on the heteroatoms consisting the heterocyclic group. These compounds are illustrated as follows:

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](3,5-dimethylisoxazol-4-yl)carboxamide.

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](benzo[d]isoxazol-3-yl)carboxamide.

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(4-methyl-1,2,3-thiadiazol-5-yl)carboxamide.

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-ethyl-5-methylisoxazol-4-yl)carboxamide.

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methyl-1-phenylpyrazol-4-yl)carboxamide.

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methoxyisoxazol-5-yl)carboxamide.

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[3-(methylethoxy)isoxazol-5-yl]carboxamide.

N-[(1S)-2-((2S)-2-{N-[(1S)-3,3,3-trifluoro-1-(methyl-ethyl)-2-oxopropyl]carbamoyl}pyrrolidinyl)-1-(methyl-ethyl)-2-oxoethyl]-(5-methylisoxazol-3-yl)carboxamide.

N-[(1S)-2-((2S)-2-{N-[(1S)-3,3,3-trifluoro-1-(methyl-ethyl)-2-oxopropyl]carbamoyl}pyrrolidinyl)-1-(methyl-ethyl)-2-oxoethyl]-(5,6-dimethylbenzo[d]isoxazol-3-yl)carboxamide.

N-[(1S)-2-((2S)-2-{N-[(1S)-3,3,3-trifluoro-1-(methyl-ethyl)-2-oxopropyl]carbamoyl}pyrrolidinyl)-1-(methyl-ethyl)-2-oxoethyl]-[1-(4-chlorophenyl)-5-methylpyrazol-4-yl]carboxamide.

N-[(1S)-2-((2S)-2-{N-[(1S)-3,3,3-trifluoro-1-(methyl-ethyl)-2-oxopropyl]carbamoyl}pyrrolidinyl)-1-(methyl-ethyl)-2-oxoethyl]-[5-methyl-1-(4-methoxyphenyl)pyrazol-4-yl]carboxamide.

N-[(1S)-2-((2S)-2-{N-[(1S)-3,3,3-trifluoro-1-(methyl-ethyl)-2-oxopropyl]carbamoyl}pyrrolidinyl)-1-(methyl-ethyl)-2-oxoethyl]-[1-(2-fluorophenyl)-5-methylpyrazol-4-yl]carboxamide.

N-[(1S)-2-((2S)-2-{N-[(1S)-3,3,3-trifluoro-1-(methyl-ethyl)-2-oxopropyl]carbamoyl}pyrrolidinyl)-1-(methyl-ethyl)-2-oxoethyl]-{5-methyl-1-[4-(trifluoromethyl)phenyl]pyrazol-4-yl}carboxamide.

The salt of the compound (I) of the present invention is not limited, but preferably a pharmaceutically acceptable salt, for example, a salt with an organic base such as trimethylamine, triethylamine, N-methylmorpholine and a salt with an inorganic metal such as sodium or potassium. Furthermore, several compounds of the compounds of the present invention form an acid addition salt with an organic acid such as tartaric acid, fumaric acid, acetic acid, lactic acid, succinic acid, methanesulfonic acid, maleic acid, malonic acid, gluconic acid, or an amino acid such as asparatic acid, or an acid additional salt with an inorganic acid such as hydrochloric acid, phosphoric acid, etc.

The compound (I) of the present invention may be in the form of a hydrate or a solvate. Furthermore, the compound (I) of the present invention exists in the form of an optically active compound, a stereoisomer or a mixture thereof, and all of them are included in the compound of the present invention.

Process for Preparation of the Compound of the Present Invention:

The compound of the present invention is novel and can be prepared, for example by the following method.

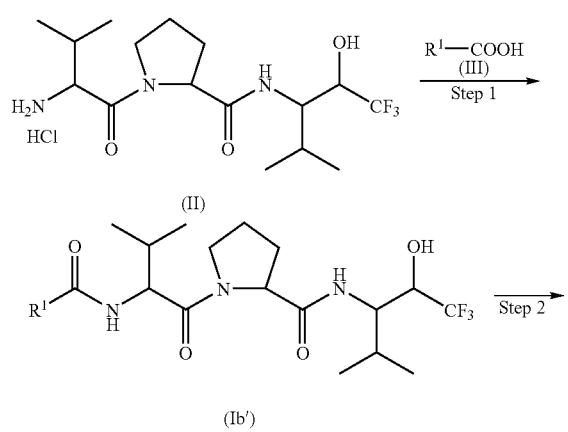

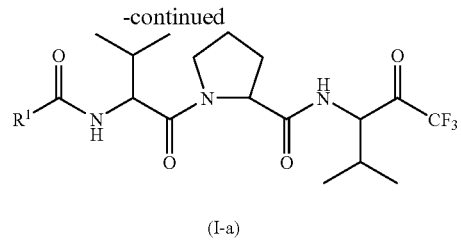

wherein $R^1$ is the same as defined above.

Step 1:

The step 1 is a step for preparation of compound (I-b') by reacting compound (II) and compound (III). This step is carried out by mixing with stirring compound (II) and compound (III) in the presence or absence of a base such as triethylamine without a solvent or in a solvent such as pyridine, dichloromethane or dimethylformamide. This step is carried out preferably, in the presence of a condensing agent such as 1-ethyl-3-(3-dimethylaminopropyl)carbodiimido hydrochloride, N,N'-dicyclohexylcarbodiimide, 1,1'-carbohyldiimidazole or N,N'-disuccinimidyl carbonate. With respect to the proportions of the quantities of the compounds (II) and (III), compound (III) may be used in the amount of 0.9 to 2 moles, preferably 0.9 to 1.5 moles per one mole of compound (II). The condensing agent may be used in the amount of 1 to 2 moles, preferably 1 to 1.5 moles per one mole of compound (II). The reaction is carried out at 0 to 40° C., preferably 0 to 25° C., for 1 to 20 hours, and preferably 2 to 15 hours.

Thus obtained compound (I-b') of the present invention (OH compound) is novel and used as a starting material in the following Step 2 for direct preparation of the compound (I-a) of the present invention (ketone compound), which is novel and useful as an elastase inhibitory agent.

The compound (II) is known and can be prepared for example, by the method described in WO 00/52032. Almost all of the compounds of the compound (III) are known, but some are novel. The said novel compounds are prepared in accordance with the method for preparation of the known compounds.

Step 2

The step 2 is a step for oxidation of hydroxy group of the compound (I-b'). The oxidation can be carried out by reacting compound (I-b') with an oxidizing agent in a solvent such as dichloromethane, dimethylformamide, tetrahydrofuran, ethyl acetate or toluene.

As the oxidizing agent, an iodobenzene derivative, namely Dess-Martin reagent is illustrated. In this step using Dess-Martin reagent, compound (I-b') is dissolved in the above solvent, and thereto are added tert-butanol (1 to 2 mole per compound (I-b')) and Dess-Martin reagent (1.5 to 3 moles, preferably 1.5 to 2.2 moles per compound (I-b')). The reaction is carried out at about 0 to 40° C., for 0.5 to 15 hours, preferably 1 to 2 hours. In addition, oxidations with diphosphorus pentaoxide in the presence of dimethyl sulfoxide, with 1-ethyl-3-(3-dimethylaminopropyl)carbodiimide or N,N'-dicyclohexylcarbodiimide hydrochloride-dichloroacetic acid ($Cl_2CHCOOH$) in the presence of dimethyl sulfoxide, and with a combination of oxalyl chloride and triethylamine (Swern oxidation) are preferably conducted, too.

The compound of the present invention is isolated from the reaction mixture by the conventionally known method for separation and purification, for example, concentration, extraction with a solvent, filtration, recrystalization, many kinds of chromatography, etc.

Thus obtained compound of the present invention can be converted into a salt thereof, or can be subjected to desaltation by the conventional manner. When there are obtained many kinds of isomers, these isomers are separated by the conventional manner.

An optically active compound of the compound (I-a) can be conveniently prepared by using an optically active compound of the compound (II) as a starting material.

Elastase Inhibitory Agent of the Present Invention

Among of the compounds (I) of the present invention, the compounds useful as an elastase inhibitory agent are compounds (I-a) (ketone compound), more preferably compounds (I-c).

The compound (I-a) of the present invention or its salt (sometimes abbreviated as an active ingredient) shows neutrophil elastase inhibitory activity and pancreas elastase inhibitory activity in oral administration.

An effective amount of the compound (I-a) of the present invention or a salt thereof is administered to a patient suffering from a disease caused by elastase.

The compound (I-a) of the present invention or its salt is preferably orally administered. The dose much varies depending on condition, body weight, and age of a patient, etc. For example, in oral administration the dose of the active ingredient is usually about 0.5 to about 5,000 mg/60 kg of body weight/day, preferably about 5 to about 2,000 mg, more preferably 15 to 300 mg.

The compound (I-a) of the present invention or its salt is administered in the form of a conventional pharmaceutical preparation, such as a tablet, a capsule, a granule, a fine granule, a powder, an aqueous or oily solution, etc. These preparations can contain an active ingredient in the amount of more than 0.01% by weight, preferably in a rage of 0.1 to 70% by weight. These preparations may contain other therapeutically active ingredient.

These pharmaceutical preparations can be prepared by using conventional pharmaceutically acceptable components in accordance with the conventional method. The components for preparing the preparations can be used as long as they are conventionally used in this field and do not react with the active ingredient such as lactose, inositol, glucose, mannitol, dextran, cyclodextrin, sorbitol, starch, partially pregelatinized starch, sucrose, magnesium aluminometasilicate, synthetic aluminum silicate, crystalline cellulose, sodium carboxymethylcellulose, hydroxypropyl starch, calcium carboxymethylcellulose, ion-exchange resin, methyl cellulose, gelatin, gum arabic, hydroxypropyl cellulose (HPC), low substituted hydroxypropyl cellulose (low substituted HPC), hydroxypropyl methyl cellulose, polyvinyl pyrrolidone, polyvinyl alcohol, alginic acid, sodium alginate, light anhydrous silicic acid, magnesium stearate, talc, carboxyvinyl polymer, titanium oxide, sorbitan fatty acid ester, sodium lauryl sulfate, glycerin, glycerin fatty acid ester, purified lanolin, glycerogelatin, polysolvate, macrogol, vegetable oil, wax, propylene glycol, water, ethanol, hydrogenated polyoxyethylene castor oil, sodium chloride, sodium hydroxide, hydrogen chloride, sodium hydrogenphosphate, sodium dihydrogenphosphate, citric acid, glutamic acid, benzyl alcohol, methyl paraoxybenzoate, ethyl paraoxybenzoate, etc.

EXAMPLE

By illustrating Examples, Experiments and Examples on preparation, the present invention is explained more in detail.

Example 1

Process for preparation of N-[(1S)-2-((2S)-2-{N-[(1S)-3,3,3-trifluoro-1-(methylethyl)-2-oxopropyl] carbamoyl}pyrrolidinyl)-1-(methylethyl)-2-oxoethyl](3,5-dimethylisoxazol-4-yl)carboxamide

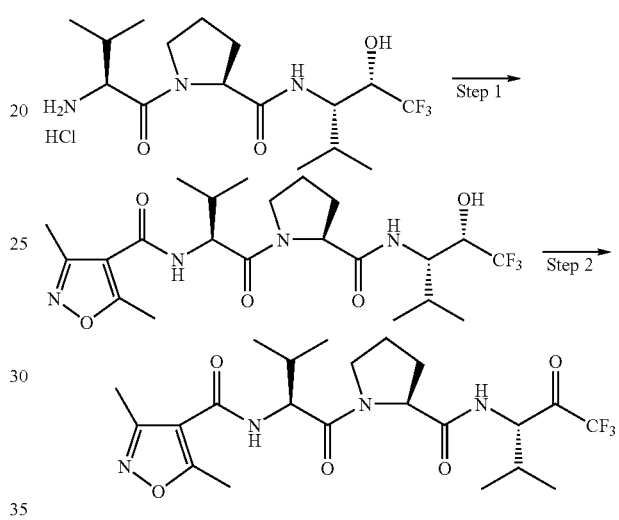

Step 1: Process for preparation of N-[(1S)-2-((2S)-2-{N-[(1S,2S)-3,3,3-trifluoro-2-hydroxy-1-(methylethyl)propyl] carbamoyl}pyrrolidinl)-1-(methylethyl)-2-oxoethyl](3,5-dimethylisoxazol-4-yl)carboxamide:

[(2S)-1-((2S)-2-amino-3-methylbutanoyl)pyrrolidin-2-yl]-N-[(1S,2S)-3,3,3-trifluoro-2-hydroxy-1-(methylethyl) propyl]carboxamide hydrochloride, a starting material of the step 1 was prepared in accordance of the method disclosed in WO 00/52032.

Thus obtained [(2S)-1-((2S)-2-amino-3-methylbutanoyl) pyrrolidin-2-yl]-N-[(1S,2S)-3,3,3-trifluoro-2-hydroxy-1-(methylethyl)propyl]carboxamide hydrochloride (2.0 g, 4.95 mmol) and 3,5-dimethylisoxazole-4-carboxylic acid (0.70 g, 4.95 mmol) were dissolved in pyridine (20 ml), and thereto was added 1-ethyl-3-(3-dimethylaminopropyl) carbodiimide hydrochloride (1.00 g, 5.20 mmol). The mixture was stirred for 12 hours at room temperature and then, the reaction mixture was concentrated under reduced pressure.

To the residue was added ethyl acetate and the mixture was washed successively with 1N hydrochloric acid, water, a saturated aqueous sodium hydrogencarbonate solution and a saturated aqueous sodium chloride solution, and dried over anhydrous sodium sulfate. The solvent was removed under reduced pressure and the residue was dissolved in acetonitrile. The solution was purified by medium pressure column chromatography using CHP-20P column (eluent: water-acetonitrile). The fraction containing the object compound was evaporated to dryness under reduced pressure to give the object compound 1.90 g (78%).

APCI-MS: 491(MH⁺)

$^1$H-NMR (300 MHz, CDCl$_3$, δ): 0.86–1.08 (12H, m), 1.94–2.35 (6H, m), 2.46 (3H, s), 2.62 (3H, s), 3.63–3.83 (2H, m), 4.07–4.13 (2H, m), 4.50–4.55 (2H, m), 4.79–4.83 (1H, m), 6.36 (1H, d), 6.72 (1H, d)

Step 2: Process for preparation of N-[(1S)-2-((2S)-2-{N-[(1S)-3,3,3-trifluoro-1-(methylethyl)-2-oxopropyl]carbamoyl}pyrrolidinyl)-1-(methylethyl)-2-oxo ethyl](3,5-dimethylisoxazol-4-yl)carboxamide:

The compound (1.90 g, 3.87 mmol) prepared in step 1 was dissolved in dichloromethane (25 ml), and thereto were added tert-butanol (0.39 ml, 3.87 mmol) and Dess-Martin reagent (3.30 g, 7.75 mmol). The mixture was stirred at room temperature for 1 hour and then, concentrated under reduced pressure. To the residue was added ethyl acetate. The mixture was washed successively with a saturated aqueous sodium thiosulfate solution, a saturated aqueous sodium hydrogencarbonate solution and a saturated aqueous sodium chloride solution, dried over anhydrous sodium sulfate, and the solvent was removed under reduced pressure. The residue was dissolved in acetonitrile and purified by medium pressure column chromatography using CHP-20P column (eluent: water-acetonitrile). The fraction containing the object compound was evaporated to dryness under reduced pressure to give the object compound 1.50 g (79%).

APCI-MS: 489(MH⁺)

$^1$H-NMR (300 MHz, CDCl$_3$, δ): 0.90–1.09 (12H, m), 1.89–2.16 (6H, m), 2.47 (3H, s), 2.64 (3H, s), 3.62–3.84 (2H, m), 4.59–4.62 (1H, m), 4.80–4.89 (2H, m), 6.36 (1H, d), 7.31 (1H, d)

Elemental Analysis for C$_{22}$H$_{31}$F$_3$N$_4$O$_5$.0.25H$_2$O Calcd.: C, 53.60; H, 6.44; F, 11.56; N, 11.36.

Found: C, 53.74; H, 6.46; F, 11.73; N, 11.24.

Examples 2 to 48

The following compounds were prepared in the same manner as Example 1. The physical properties of the compounds were shown in Table 1. Mass spectrum in the table was measured by APCIMS unless otherwise specified.

Example 2

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](benzo [d]isoxazol-3-yl)carboxamide Example 3

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(4-methyl-1,2,3-thiadiazol-5-yl)carboxamide Example 4

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-ethyl-5-methylisoxazol-4-yl)carboxamide Example 5

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3,5-dimethylisothiazol-4-yl)carboxamide Example 6

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1,5-dimethylpyrazol-3-yl)carboxamide Example 7

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](benzotriazol-5-yl)carboxamide Example 8

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1H-indazol-3-yl)carboxamide.

Example 9

N-[(1S)-2-((2S)-2-(N-[(1S)-3,3,3-trifluoro-1-(methylethyl)-2-oxopropyl]carbamoyl}pyrrolidinyl)-1-(methylethyl)-2-oxoethyl]-(5-phenylisoxazol-3-yl)carboxamide Example 10

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methyl-1-phenylpyrazol-4-yl)carboxamide Example 11

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methoxyisoxazol-5-yl)carboxamide Example 12

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[3-(methylethoxy)isoxazol-5-yl]carboxamide Example 13

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[1-(methylethyl)benzotriazol-5-yl]carboxamide Example 14

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](benzo[d]1,2,3-thiadiazol-5-yl)carboxamide Example 15

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methylisoxazol-3-yl)carboxamide

Example 16

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3,5-dimethylpyrazol-4-yl)carboxamide

Example 17

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5,6-dimethylbenzo[d]isoxazol-3-yl)carboxamide

Example 18

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methylbenzo[d]isoxazol-3-yl)carboxamide

Example 19

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methoxyisoxazol-4-yl)carboxamide

Example 20

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methylisoxazol-4-yl)carboxamide

Example 21

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methylisoxazol-4-yl)carboxamide

Example 22

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methylisoxazol-5-yl)carboxamide

Example 23

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-tert-butylisoxazol-5-yl)carboxamide

Example 24

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-phenylisoxazol-5-yl)carboxamide

Example 25

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-tert-butyl-1-methylpyrazol-3-yl)carboxamide

Example 26

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-methyl-5-phenylpyrazol-3-yl)carboxamide

Example 27

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-tert-butyl-5-methylpyrazol-3-yl)carboxamide

Example 28

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-phenylpyrazol-3-yl)carboxamide

Example 29

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methyl-1-phenylpyrazol-3-yl)carboxamide

Example 30

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-tert-butyl-1-phenylpyrazol-3-yl)carboxamide

Example 31

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1,3-dimethylpyrazol-5-yl)carboxamide

Example 32

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-tert-butyl-5-methylpyrazol-4-yl)carboxamide

Example 33

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-phenylpyrazol-4-yl)carboxamide

Example 34

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3,5-dimethyl-1-phenylpyrazol-4-yl)carboxamide

Example 35

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-methyl-3-phenylpyrazol-5-yl)carboxamide

Example 36

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methyl-1-phenylpyrazol-5-yl)carboxamide

Example 37

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[1-(4-fluorophenyl)-5-methylpyrazol-4-yl]carboxamide

Example 38

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[1-(4-chlorophenyl)-5-methylpyrazol-4-yl]carboxamide

Example 39

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[5-methyl-1-(4-methylphenyl) pyrazol-4-yl]carboxamide

Example 40

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[5-methyl-1-(4-methoxyphenyl)pyrazol-4-yl]carboxamide

Example 41

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-tert-butyl-1-methylpyrazol-5-yl)carboxamide

Example 42

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-tert-butyl-3-methylpyrazol-5-yl)carboxamide

Example 43

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[(3-methylethoxy)isoxazol-4-yl]carboxamide

Example 44

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-tert-butyl-1-phenylpyrazol-5-yl)carboxamide

Example 45

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-1-(2-fluorophenyl)-5-methylpyrazol-4-yl]carboxamide

Example 46

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[1-(3-fluorophenyl)-5-methylpyrazol-4-yl]carboxamide

Example 47

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-{5-methyl-1-[4-(trifluoromethyl)phenyl]pyrazol-4-yl}carboxamide

Example 48

N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-{5-methyl-1-[3-(trifluoromethyl)phenyl]pyrazol-4-yl}carboxamide

TABLE 1

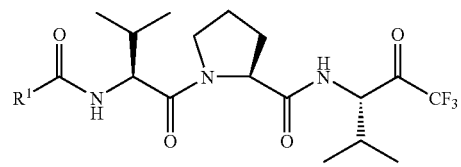

| Example No. | $R^1$ | $MH^+$ | Elemental analysis Calc.(Found) |
|---|---|---|---|
| Example 2 | 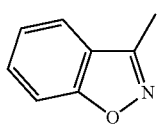 | 511 LSIMS | $C_{24}H_{29}F_3N_4O_5$: C 56.47(56.29), H 5.73(5.70), F 11.16(11.17), N 10.97 (10.91) |

TABLE 1-continued
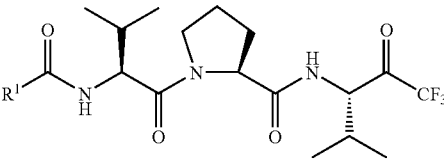
| Example No. | R¹ | MH⁺ | Elemental analysis Calc.(Found) |
|---|---|---|---|
| Example 3 | 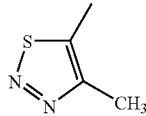 | 492 | $C_{20}H_{28}F_3N_5O_4S$: C 48.87(48.81), H 5.74(5.98), F 11.60(11.48), N 14.25(14.14), S 6.52(6.37) |
| Example 4 | 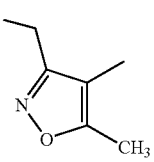 | 503 LSIMS | $C_{23}H_{33}F_3N_4O_5$: C 54.97(54.91), H 6.62(6.74), F 11.34(11.17), N 11.15(10.93) |
| Example 5 | 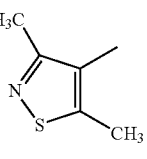 | 505 LSIMS | $C_{22}H_{31}F_3N_4O_4S$: C 52.37(52.20), H 6.19(6.16), F 11.30(11.30), N 11.10(10.95), S 6.36(6.22) |
| Example 6 | 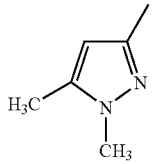 | 488 LSIMS | $C_{22}H_{32}F_3N_5O_4 \cdot 0.25H_2O$: C 53.70(53.77), H 6.66(6.76), F 11.58(11.34), N 14.23(14.47) |
| Example 7 | 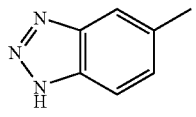 | 511 | $C_{25}H_{30}F_3N_5O_4$: C 54.11(53.92), H 5.73(5.76), F 11.16(10.99), N 16.46(16.31) |
| Example 8 | 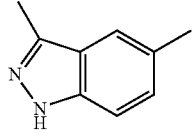 | 510 | $C_{24}H_{30}F_3N_5O_4 \cdot 0.45H_2O \cdot 0.05AcOEt$: C 55.68(55.68), H 6.04(5.94), F 10.92(10.79), N 13.42(13.13) |
| Example 9 | 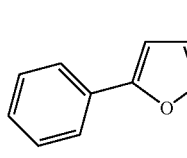 | 537 | $C_{26}H_{31}F_3N_4O_5 \cdot 0.25H_2O$: C 57.72(57.71), H 5.87(5.85), F 10.53(10.49), N 10.36(10.34) |
| Example 10 | 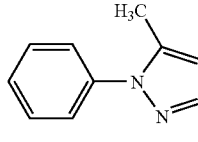 | 550 | $C_{27}H_{34}F_3N_5O_4 \cdot 0.25H_2O$: C 58.53(58.23), H 6.28(6.08), F 10.29(10.16), N 12.64(12.54) |
| Example 11 | 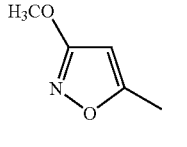 | 491 | $C_{21}H_{29}F_3N_4O_6$: C 51.42(51.14), H 5.96(6.17), F 11.62(11.39), N 11.42(11.12) |

TABLE 1-continued
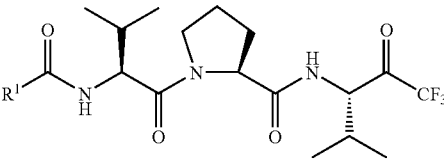
| Example No. | R¹ | MH⁺ | Elemental analysis Calc.(Found) |
|---|---|---|---|
| Example 12 | 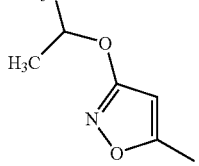 | 519 | $C_{23}H_{33}F_3N_4O_6$: C 53.28(53.02), H 6.41(6.26), F 10.99(10.73), N 10.81(10.68) |
| Example 13 | 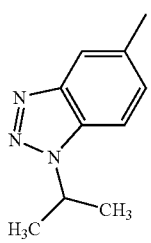 | 553 LSIMS | $C_{26}H_{35}F_3N_6O_4 \cdot 0.25H_2O$: C 56.05(55.75), H 6.42(6.51), F 10.23(10.18), N 15.09(14.92) |
| Example 14 | 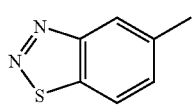 | 528 LSIMS | $C_{23}H_{28}F_3N_5O_4S \cdot 0.30H_2O$: C 51.83(51.95), H 5.41(5.43), F 10.69(10.40), N 13.14(13.04), S 6.02(5.85) |
| Example 15 | 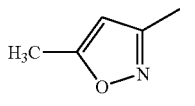 | 475 | $C_{21}H_{29}F_3N_4O_5 \cdot 0.25H_2O$: C 52.66(52.56), H 6.21(6.06), F 11.90(11.81), N 11.70(11.69) |
| Example 16 | 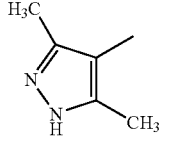 | 488 | $C_{22}H_{32}F_3N_5O_4 \cdot 0.50H_2O$: C 53.22(53.51), H 6.70(6.56), F 11.48(11.34), N 14.10(13.82) |
| Example 17 | 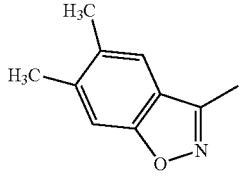 | 539 LSIMS | $C_{26}H_{33}F_3N_4O_5 \cdot 0.25H_2O$: C 57.50(57.60), H 6.22(6.26), F 10.50(10.42), N 10.32(10.24) |
| Example 18 | 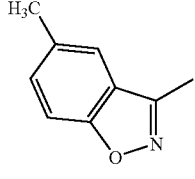 | 525 LSIMS | $C_{25}H_{31}F_3N_4O_5 \cdot 0.25H_2O$: C 56.76(56.50), H 6.00(6.04), F 10.77(10.58), N 10.59(10.50) |
| Example 19 | 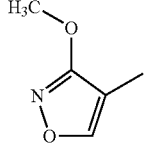 | 491 | $C_{21}H_{29}F_3N_4O_6 \cdot 0.5H_2O$: C 50.50(50.53), H 6.05(6.07), F 11.41(11.44), N 11.22(11.14) |

TABLE 1-continued

| Example No. | R¹ | MH⁺ | Elemental analysis Calc.(Found) |
|---|---|---|---|
| Example 20 | 4,5-dimethylisoxazol-3-yl | 475 | $C_{21}H_{29}F_3N_4O_5$: C 53.16(52.87), H 6.16(6.22), F 12.01(11.90), N 11.81(11.66) |
| Example 21 | 3,4-dimethylisoxazol-5-yl | 475 | $C_{21}H_{29}F_3N_4O_5 \cdot 0.25H_2O$: C 52.66(52.63), H 6.21(6.20), F 11.70(11.70), N 11.90(11.61) |
| Example 22 | 3,5-dimethylisoxazol-4-yl | 475 | $C_{21}H_{29}F_3N_4O_5$: C 53.16(53.08), H 6.16(6.32), F 12.01(11.75), N 11.81(11.62) |
| Example 23 | 3-tert-butyl-5-methylisoxazol-4-yl | 517 | $C_{24}H_{35}F_3N_4O_5 \cdot 0.25H_2O$: C 55.32(55.22), H 6.87(6.91), F 10.94(10.83), N 10.75(10.56) |
| Example 24 | 5-methyl-3-phenylisoxazol-4-yl | 537 | $C_{26}H_{31}F_3N_4O_5 \cdot 0.25H_2O$: C 57.72(57.59), H 5.87(5.95), F 10.53(10.29), N 10.36(10.15) |
| Example 25 | 5-tert-butyl-1,3-dimethylpyrazol-4-yl | 530 | $C_{25}H_{38}F_3N_5O_4$: C 56.70(56.43), H 7.23(7.44), F 10.56(10.76), N 13.00(13.22) |
| Example 26 | 1-methyl-3-methyl-5-phenylpyrazol-4-yl | 550 | $C_{27}H_{34}F_3N_5O_4 \cdot 0.25H_2O$: C 58.53(58.30), H 6.28(6.29), F 10.29(10.18), N 12.64(12.51) |
| Example 27 | 1-tert-butyl-3,5-dimethylpyrazol-4-yl | 530 | $C_{25}H_{38}F_3N_5O_4 \cdot 0.5H_2O$: C 55.75(55.87), H 7.30(7.32), F 10.58(10.28), N 13.00(12.98) |
| Example 28 | 3-methyl-1-phenylpyrazol-4-yl | 536 | $C_{26}H_{32}F_3N_5O_4 \cdot 0.25H_2O$: C 57.82(57.55), H 6.07(5.98), F 12.97(12.79), N 10.55(10.38) |

TABLE 1-continued
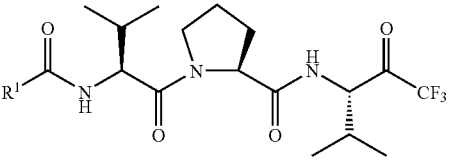
| Example No. | R¹ | MH⁺ | Elemental analysis Calc.(Found) |
|---|---|---|---|
| Example 29 | 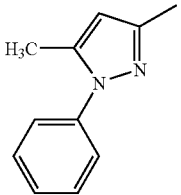 | 550 | $C_{27}H_{34}F_3N_5O_4 \cdot 0.25H_2O$:<br>C 58.53(58.37),<br>H 6.28(6.25), F 10.29(10.22),<br>N 12.64(12.57) |
| Example 30 | 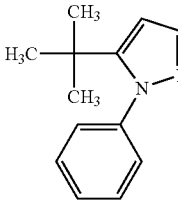 | 592 | $C_{30}H_{40}F_3N_5O_4 \cdot 0.25H_2O$:<br>C 60.44(60.24),<br>H 6.85(6.81), F 9.56(9.44),<br>N 11.75(11.49) |
| Example 31 | 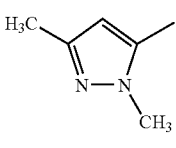 | 488 | $C_{22}H_{32}F_3N_5O_4 \cdot 0.5H_2O$:<br>C 53.22(53.31),<br>H 6.70(6.55), F 11.48(11.37),<br>N 14.10(13.94) |
| Example 32 | 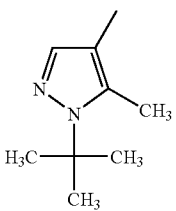 | 530 | $C_{25}H_{38}F_3N_5O_4 \cdot 0.75H_2O$:<br>C 55.29(55.41),<br>H 7.33(7.31), F 10.49(10.28),<br>N 12.89(12.80) |
| Example 33 | 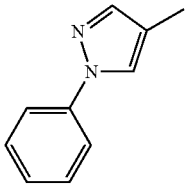 | 536 | $C_{26}H_{32}F_3N_5O_4 \cdot 0.25H_2O$:<br>C 57.82(57.91),<br>H 6.07(6.02), F 10.55(10.50),<br>N 12.97(12.96) |
| Example 34 | 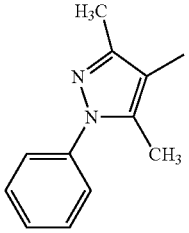 | 564 | $C_{28}H_{36}F_3N_5O_4 \cdot 0.25H_2O$:<br>C 59.20(59.09),<br>H 6.48(6.43), F 10.03(9.99),<br>N 12.33(12.32) |

TABLE 1-continued
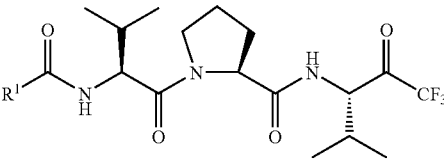
| Example No. | R¹ | MH⁺ | Elemental analysis Calc.(Found) |
|---|---|---|---|
| Example 35 | 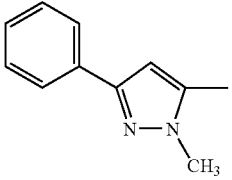 | 550 | $C_{27}H_{34}F_3N_5O_4 \cdot 0.25H_2O$:<br>C 58.53(58.58),<br>H 6.28(6.23), F 10.29(10.30),<br>N 12.64(12.67) |
| Example 36 | 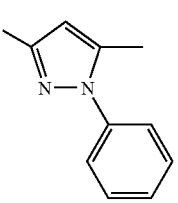 | 550 | $C_{27}H_{34}F_3N_5O_4 \cdot 0.25H_2O$:<br>C 58.53(58.37),<br>H 6.28(6.30),<br>F 10.29(10.34),<br>N 12.64(12.41) |
| Example 37 | 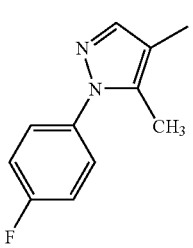 | 568 | $C_{27}H_{33}F_4N_5O_4 \cdot 0.25H_2O$:<br>C 56.69(56.58),<br>H 5.90(5.98), F 13.28(13.23),<br>N 12.24(12.26) |
| Example 38 | 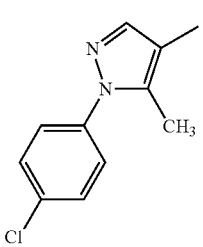 | 585 | $C_{27}H_{33}ClF_3N_5O_4 \cdot 0.25H_2O$:<br>C 55.10(54.86),<br>H 5.74(5.69), Cl 6.02(5.98),<br>F 9.68(9.64), N 11.90(11.86) |
| Example 39 | 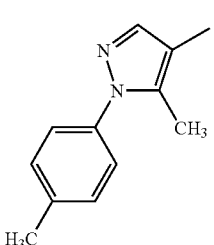 | 564 | $C_{28}H_{36}F_3N_5O_4 \cdot 0.5H_2O$:<br>C 58.73(58.76),<br>H 6.51(6.38), F 9.95(10.01),<br>N 12.23(12.27) |
| Example 40 | 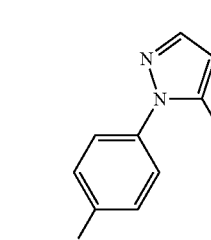 | 580 | $C_{28}H_{36}F_3N_5O_5 \cdot 0.25H_2O$:<br>C 57.57(57.39),<br>H 6.30(6.26), F 9.76(9.58),<br>N 11.99(11.73) |

TABLE 1-continued
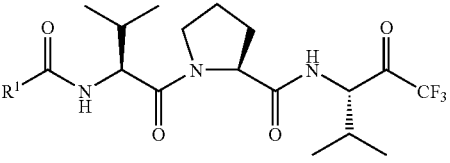
| Example No. | R¹ | MH⁺ | Elemental analysis Calc.(Found) |
|---|---|---|---|
| Example 41 | 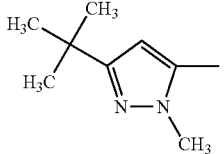 | 530 | $C_{25}H_{38}F_3N_5O_4 \cdot 0.25H_2O \cdot 0.25AcOEt$: C 56.15(56.11), H 7.34(7.44), F 10.25(10.34), N 12.59(12.62) |
| Example 42 | 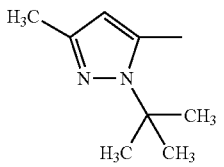 | 530 | $C_{25}H_{38}F_3N_5O_4 \cdot 0.5H_2O$: C 55.75(55.90), H 7.30(7.31), F 10.58(10.58), N 13.00(12.96) |
| Example 43 | 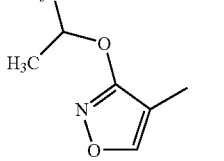 | 519 | $C_{23}H_{33}F_3N_4O_6 \cdot 0.5H_2O$: C 52.37(52.32), H 6.50(6.49), F 10.80(10.80), N 10.62(10.54) |
| Example 44 | 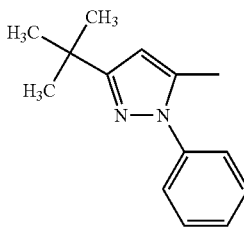 | 592 | $C_{30}H_{40}F_3N_5O_4 \cdot 0.75H_2O$: C 59.54(59.84), H 6.91(6.72), F 9.42(9.12), N 11.57(11.25) |
| Example 45 | 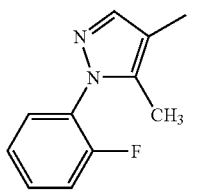 | 568 | $C_{27}H_{33}F_4N_5O_4 \cdot 0.25H_2O$: C 56.69(56.55), H 5.90(5.83), F 13.28(13.23), N 12.24(12.15) |
| Example 46 | 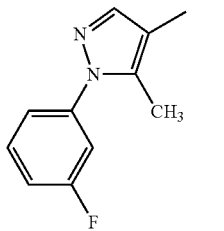 | 568 | $C_{27}H_{33}F_4N_5O_4 \cdot 0.5H_2O$: C 56.24(56.38), H 5.94(5.96), F 13.18(13.13), N 12.15(12.12) |

TABLE 1-continued

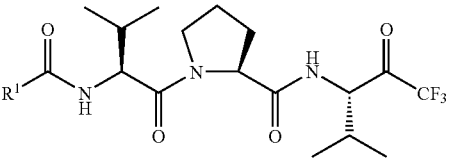

| Example No. | R[1] | MH+ | Elemental analysis Calc.(Found) |
|---|---|---|---|
| Example 47 | 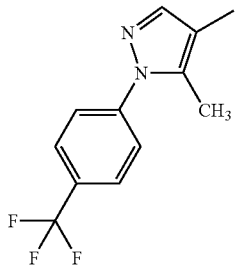 | 618 | $C_{28}H_{33}F_6N_5O_4 \cdot 0.5H_2O$:<br>C 53.67(53.63), H 5.47(5.41),<br>F 18.19(18.01),<br>N 11.18(11.18) |
| Example 48 | 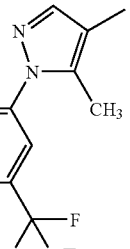 | 618 | $C_{28}H_{33}F_6N_5O_4 \cdot 0.5H_2O$:<br>C 53.67(53.60), H 5.47(5.43),<br>F 18.19(18.19),<br>N 11.18(11.15) |

Example 49

The following compounds can be prepared in the same manner as Example 1.

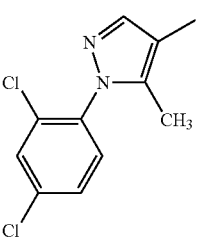

| R[1] | Chemical name |
|---|---|
|  | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,4-dichlorophenyl)-5-methylpyrazol-4-yl)carboxamide |

-continued

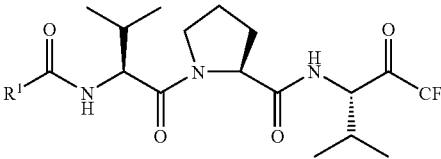

| R[1] | Chemical name |
|---|---|
| 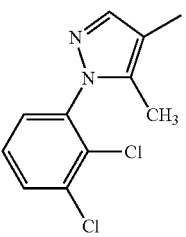 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,3-dichlorophenyl)-5-methylpyrazol-4-yl)carboxamide |
| 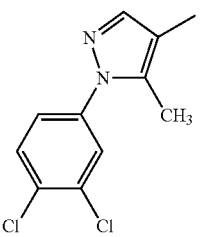 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3,4-dichlorophenyl)-5-methylpyrazol-4-yl)carboxamide |
| 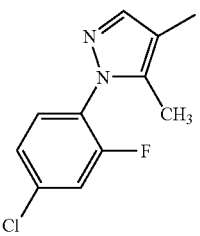 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-chloro-2-fluorophenyl)-5-methylpyrazol-4-yl)carboxamide |
| 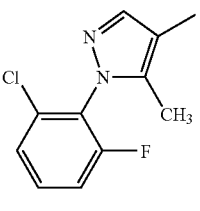 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2-chloro-6-fluorophenyl)-5-methylpyrazol-4-yl)carboxamide |
| 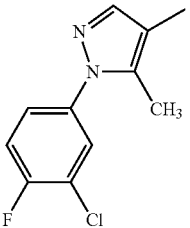 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3-chloro-4-fluorophenyl)-5-methylpyrazol-4-yl)carboxamide |
| 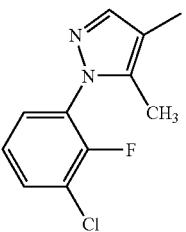 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3-chloro-2-fluorophenyl)-5-methylpyrazol-4-yl)carboxamide |

-continued

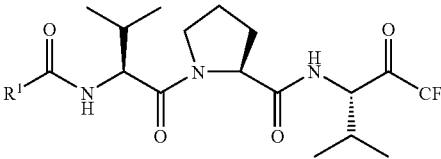

| R¹ | Chemical name |
|---|---|
| 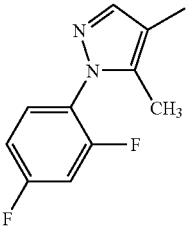 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,4-difluorophenyl)-5-methylpyrazol-4-yl)carboxamide |
| 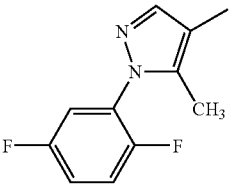 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,5-difluorophenyl)-5-methylpyrazol-4-yl)carboxamide |
| 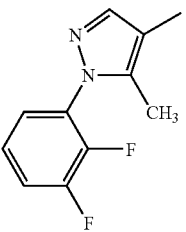 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,3-difluorophenyl)-5-methylpyrazol-4-yl)carboxamide |
| 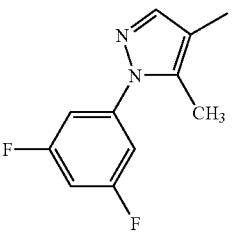 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3,5-difluorophnyl)-5-methylpyrazol-4-yl)carboxamide |
| 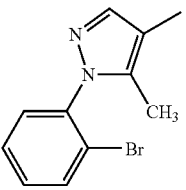 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2-bromophenyl)-5-methylpyrazol-4-yl)carboxamide |
| 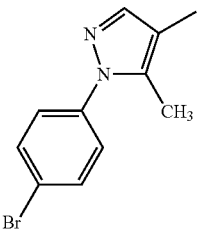 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-bromophenyl)-5-methylpyrazol-4-yl)carboxamide |

-continued

| R¹ | Chemical name |
|---|---|
| 4-bromo-2-fluorophenyl-substituted 5-methylpyrazol-4-yl (with CH₃ on pyrazole) | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-bromo-2-fluorophenyl)-5-methylpyrazol-4-yl)carboxamide |
| 3-methoxyphenyl-substituted 5-methylpyrazol-4-yl | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3-methoxyphenyl)-5-methylpyrazol-4-yl)carboxamide |
| 2-methoxyphenyl-substituted 5-methylpyrazol-4-yl | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2-methoxyphenyl)-5-methylpyrazol-4-yl)carboxamide |
| 3-chloro-4-methoxyphenyl-substituted 5-methylpyrazol-4-yl | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3-chloro-4-methoxyphenyl)-5-methylpyrazol-4-yl)carboxamide |
| 4-chloro-2-methoxyphenyl-substituted 5-methylpyrazol-4-yl | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-chloro-2-methoxyphenyl)-5-methylpyrazol-4-yl)carboxamide |
| 2-methyl-4-methoxyphenyl-substituted 5-methylpyrazol-4-yl | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2-methyl-4-methoxyphenyl)-5-methylpyrazol-4-yl)carboxamide |

-continued

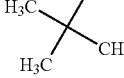

| R[1] | Chemical name |
|---|---|
| 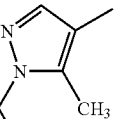 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-tert-butylphenyl)-5-methylpyrazol-4-yl)carboxamide |
| 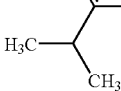 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-iso-propylphenyl)-5-methylpyrazol-4-yl)carboxamide |
| 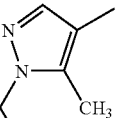 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3-chloro-4-methylphenyl)-5-methylpyrazol-4-yl)carboxamide |
| 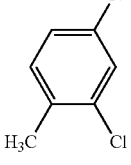 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-chloro-3-methylphenyl)-5-methylpyrazol-4-yl)carboxamide |
| 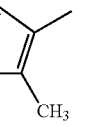 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(3-ethoxy-isoxazol-5-yl)carboxamide |
| 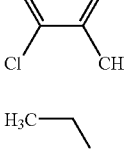 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(3-tert-butoxy-isoxazol-5-yl)carboxamide |

-continued

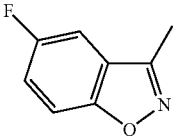

| R¹ | Chemical name |
|---|---|
| 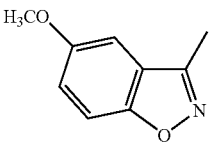 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-fluoro-benzo[d]isoxazol-3-yl)carboxamide |
| 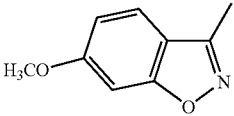 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-methoxybenzo[d]isoxazol-3-yl)carboxamide |
| 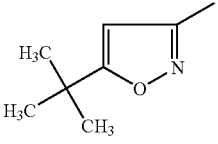 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(6-methoxybenzo[d]isoxazol-3-yl)carboxamide |
| 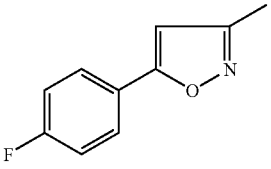 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-(tert-butyl)isoxazol-3-yl)carboxamide |
| 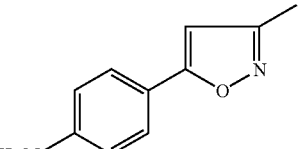 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-(4-fluorophenyl)isoxazol-3-yl)carboxamide |
| 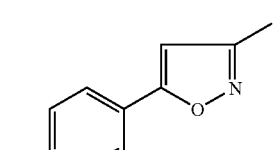 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-(4-methoxyphenyl)isoxazol-3-yl)carboxamide |
| 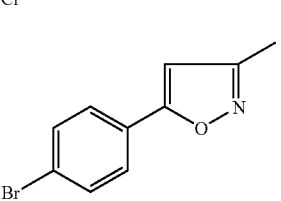 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-(4-chlorophenyl)isoxazol-3-yl)carboxamide |
| | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-(4-bromophenyl)isoxazol-3-yl)carboxamide |

-continued

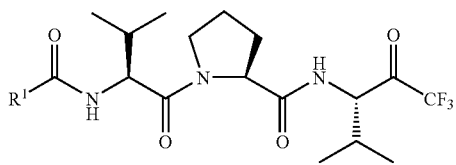

| R[1] | Chemical name |
|---|---|
| 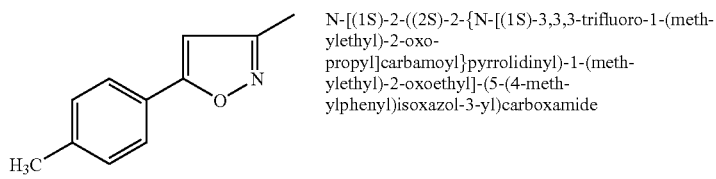 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(5-(4-methylphenyl)isoxazol-3-yl)carboxamide |
| 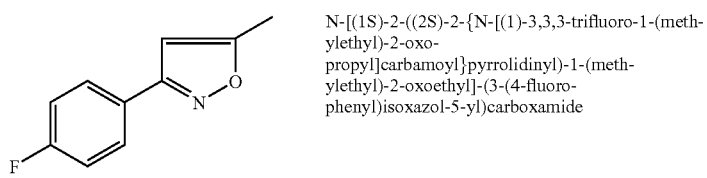 | N-[(1S)-2-((2S)-2-{N-[(1)-3,3,3-trifluoro-1-(methylethyl)-2-oxo-propyl]carbamoyl}pyrrolidinyl)-1-(methylethyl)-2-oxoethyl]-(3-(4-fluorophenyl)isoxazol-5-yl)carboxamide |
| 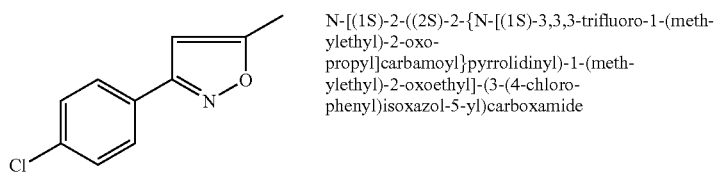 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(3-(4-chlorophenyl)isoxazol-5-yl)carboxamide |
| 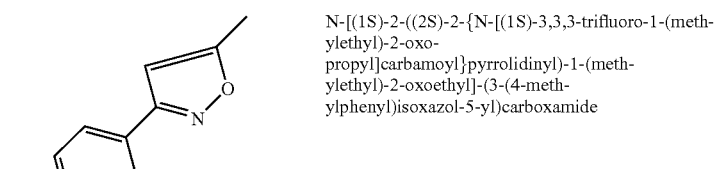 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(3-(4-methylphenyl)isoxazol-5-yl)carboxamide |
| 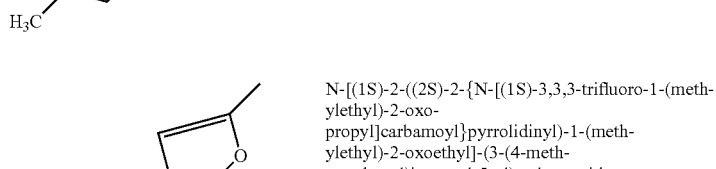 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(3-(4-methoxyphenyl)isoxazol-5-yl)carboxamide |
| 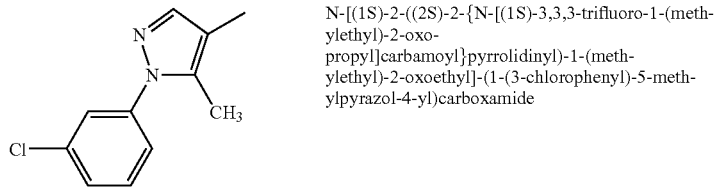 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3-chlorophenyl)-5-methylpyrazol-4-yl)carboxamide |

-continued

| R¹ | Chemical name |
|---|---|
| 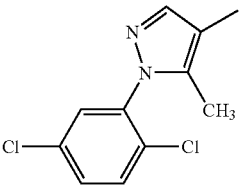 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,5-dichlorophenyl)-5-methylpyrazol-4-yl)carboxamide |
| 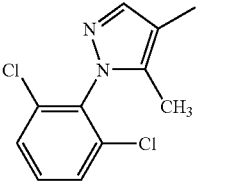 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(2,6-dichlorophenyl)-5-methylpyrazol-4-yl)carboxamide |
| 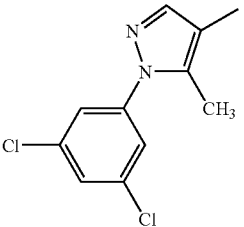 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(3,5-dichlorophenyl)-5-methylpyrazol-4-yl)carboxamide |
| 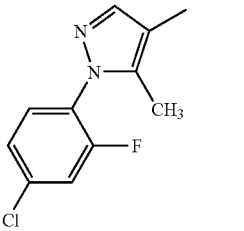 | N-[(1S)-2-((2S)-2-{N-[(1S)-3,3,3-trifluoro-1-(methylethyl)-2-oxo-propyl]carbamoyl}pyrrolidinyl)-1-(methylethyl)-2-oxoethyl]-(1-(4-chloro-2-fluorophenyl)-5-methylpyrazol-4-yl)carboxamide |

Experiment 1: Inhibitory Activity on Human Neutrophil Elastase (HNE)

The inhibitory activity of the compound of the present invention in vitro on human neutrophil elastase was examined by this experiment.

To 100 mM of HEPES {[N-(2-hydroxyethyl)piperazine-N'-(2-ethanesulfonic acid)], pH 7.5} buffer solution containing 1M NaCl and 0.001% Brij-35 (polyoxyethylene lauryl ether) were added human neutrophil elastase (final concentration: 0.2 U/ml, Elastine Product Co., Inc.) and the compound of the present invention (dissolved in 10% dimethyl sulfoxide; final concentration: $10^{-10} \sim 3 \times 10^{-3}$ M). The mixture was pre-incubated for 3 minutes at 37° C. Thereto was added MeO-Suc-Ala-Ala-Pro-Val-pNA (methoxysuccinyl-alanyl-alanyl-prolyl-valyl-p-nitroanilide (Sigma Chemical Co.)) as a substrate to give the final concentration of 0.5 mM, and the reaction was initiated. Under this condition, the producing rate of the reaction product, p-nitroanilide (pNA) at 37° C. was estimated by measuring the absorbance at 404 nm for 3 minutes.

The inhibitory activity of the compound of the present invention against human neutrophil elastase (HNE) is calculated according to the following formula.

$$\text{Inhibitory rate (\%)} = \left(1 - \frac{\text{Increase in absorbance in presence of compound of present invention}}{\text{Increase in absorbance in absence of compound of present invention}}\right) \times 100$$

The concentration of the compound of the present invention to be required to achieve 50% HNE inhibition (i.e., $IC_{50}$) was calculated based on the concentration-inhibitory rate curve of the compound of the present invention.

As a comparative compound, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](imidazol-4-yl)carboxamide was used, and the same assay was carried out. The planar structure of this compound was the same as one of compound (22) disclosed in J. Med. Chem., 1997, 40, 1876–1885.

The result was shown in the following Table 2.

TABLE 2

| Example No. | $IC_{50}$(nM) |
|---|---|
| Example 1 | 17 |
| Example 2 | 8.1 |
| Example 3 | 13 |
| Example 4 | 17 |
| Example 5 | 22 |
| Example 9 | 9.2 |
| Example 10 | 10 |
| Example 11 | 27 |
| Example 12 | 16 |
| Example 13 | 6.3 |
| Example 14 | 12 |
| Example 15 | 24 |
| Example 17 | 11 |
| Example 18 | 12 |
| Comparative compound | 78 |
| Example 21 | 11 |
| Example 23 | 15 |
| Example 24 | 15 |
| Example 32 | 8.5 |
| Example 33 | 12 |
| Example 34 | 9.8 |
| Example 37 | 9.1 |
| Example 38 | 8.3 |
| Example 39 | 10 |
| Example 40 | 8.4 |
| Example 45 | 8.4 |
| Example 46 | 8.1 |
| Example 47 | 15 |

As shown in Table 2, the compound of the present invention showed the potent-inhibitory activity on human neutrophil elastase.

Experiment 2: Inhibitory Activity Against Porcine Pancreas Elastase

The inhibitory activity was measured in the same manner as experiment 1, except for using porcine pancreas elastase (Elastin Products Co., Inc., final concentration 40 ng/ml) as a target enzyme and Suc-Ala-Ala-Ala-pNA (succinyl-alanyl-alanyl-alanyl-p-nitroanilide, Peptide Research, final concentration 2.5 mM) as a substrate.

The result was shown in Table 3 below.

TABLE 3

| Example No. | $IC_{50}$(nM) |
|---|---|
| Example 1 | 154 |
| Example 2 | 215 |
| Example 3 | 155 |

As show in Table 3, the compound of the present invention showed the inhibitory activity on pancreas elastase.

Experiment 3: Inhibitory Activity on Pulmonary Hemorrhage Induced by Human Neutrophil Elastase (HNE)

This experiment tested on in vivo efficacy of the compound of the present invention. When human neutrophil elastase is intratracheally administered to a hamster, the pulmonary hemorrhage is induced. A definite time later after administration of the elastase, in the bronchoalveolar lavage fluid by washing lung via trachea, hemoglobin is detected. This experiment was to estimate how potently the compound of the present invention inhibited the hemorrhage by measuring the hemoglobin concentration.

Hamsters (Syrian strain, 7–10 weeks old male) were divided into groups consisting of 3 to 6, and each group was treated as follows:

(A) A Group to which the Compound of the Present Invention was not Administered (Disease Control):

Physiological saline solution (0.2 ml) in which 25 unit of human neutrophil elastase (Elastin Product Co., Inc.) was dissolved was intratracheally administered to a hamster to induce the pulmonary hemorrhage. One hour later after administration of elastase, the hamsters were sacrificed by exsanquination, and alveoli were transtracheally washed twice with physiological saline (2.5 ml), and the hemoglobin concentration in the bronchoalveolar lavage fluid (5 ml) was determined by measuring the absorbance at 414 nm.

(B) A Group to which the Compound of the Present Invention was Administered:

A fixed amount of the compound of the present invention was dissolved in dimethyl sulfoxide (DMSO), and thereto was added 0.5% tragacanth gum to prepare a suspension. The suspension was orally administered to a hamster, 30 minutes prior to the administration of human neutrophil elastase (HNE) (final concentration of DMSO, 1%), and then, human neutrophil elastase was administered in the same manner as the above method (A). After 1 hour, the concentration of hemoglobin in the bronchoalveolar lavage fluid was determined in the same manner as the above method (A).

The hemorrhage inhibition activity of the compound of the present invention is represented as the hemorrhage inhibiting rate in the following formula.

$$\text{Hemorrhage inhibiting rate (\%)} = \left(1 - \frac{A_{414} \text{ of group of compound of present invention}}{A_{414} \text{ of group of disease control}}\right) \times 100$$

The dose of the compound of the present invention to be required to achieve 50% inhibition of pulmonary hemorrhage (i.e., $ED_{50}$) was calculated based on the administration dose-hemorrhage inhibiting rate curve.

As a comparative example, the same experiment was also carried out on a comparative compound used in Experiment 1.

Some of the compounds of the present invention were compared with the comparative compound on the hemorrhage inhibitory rate at the dose of 3 mg/kg.

The result was shown in Table 4 and Table 5.

TABLE 4

| Example No. | Inhibitory activity on pulmonary hemorrhage $ED_{50}$ (mg/kg) |
|---|---|
| Example 1 | 2.6 |
| Example 2 | 0.86 |
| Example 3 | 1.6 |
| Example 4 | 2.5 |
| Example 10 | 1.1 |
| Example 11 | 1.5 |
| Example 15 | 0.62 |
| Comparative compound | >10 |

TABLE 5

| Example No. | Pulmonary hemorrhage inhibitory rate (%) dose (3 mg/kg) |
|---|---|
| Example 12 | 66 |
| Example 17 | 59 |
| Example 38 | 63 |
| Example 40 | 70 |
| Example 45 | 58 |
| Example 47 | 60 |
| Comparative compound | 18 |

As shown in Table 4 and Table 5, the compound of the present invention showed the potent inhibitory activity on the pulmonary hemorrhage in this experiment.

Experiment 4: Duration of Inhibitors Activity on Pulmonary Hemorrhage Induced by Human Neutrophil Elastase (HNE)

The same procedure as Experiment 3 (B) was conducted except that the dose (10 mg/kg) of the compound of the present invention was orally administered 150 minutes (instead of 30 minutes) prior to the administration of human neutrophil elastase (HNE).

As a result, even though the compound of the present invention of Example 10 was administered 150 minutes prior to the administration of HNE, the compound of the present invention potently inhibited the pulmonary hemorrhage and showed the activity for longer duration.

Experiment 5: Acute Toxicity

The compound of the present invention (each compound of Example 10, Example 11, Example 15, Example 25, and Example 40) was suspended in 0.5% tragacanth gum and the suspension was orally administered to 7 weeks old, male ICR mice (5 mice) at 300 mg/kg. After 24 hours of administration, all were alive by checking death or not.

As shown in the above experiments, the compound of the present invention does not show only distinct neutrophil elastase inhibitory activity and pancreas elastase inhibitory activity in vitro, but also excellent elastase inhibitory activity in oral administration. Therefore, the compound of the present invention is useful for prophylaxis and treatment for various diseases caused by increased elastase activity, such as various diseases caused by increased protein degradation by elastase, especially respiratory diseases.

The examples on the preparation were illustrated below. The compound of the present invention, an active ingredient was used after being micronized to a size of 5 μm or below.

Examples A, B and C: Tablet

The components for granules shown in Table 6 were granulated in accordance with the conventional method and thereto were added excipients. The mixture was compressed to prepare tablets each weighing 120 mg to 300 mg.

TABLE 6

| | Component | Amount (mg) | | |
|---|---|---|---|---|
| | | Preparation A | Preparation B | Preparation C |
| Granule | Compound of example 1 | 1 | 10 | 100 |
| | Lactose | 84.2 | 75.2 | 117.5 |
| | Corn starch | — | 12 | — |
| | Low substituted HPC | 12 | — | 30 |
| | HPC | 3 | 3 | 8 |
| Excipient | Crystalline cellulose | 18 | 18 | 40 |
| | Magnesium stearate | 1.2 | 1.2 | 3.0 |
| | Light anhydrous silicic acid | 0.6 | 0.6 | 1.5 |
| | Total (mg) | 120 | 120 | 300 |

Examples D, E and F: Granules

The components for granules shown in Table 7 were granulated according to the conventional method and thereto was added an excipient to give granules.

TABLE 7

| | Component | Amount (wt. %) | | |
|---|---|---|---|---|
| | | Preparation D | Preparation E | Preparation F |
| Granule | Compound of example 1 | 1 | 10 | 50 |
| | D-mannitol | 85.5 | 76.5 | 36.5 |
| | Low substituted HPC | 10 | 10 | 10 |
| | HPC | 3 | 3 | 3 |
| Excipient | Light anhydrous silicic acid | 0.5 | 0.5 | 0.5 |
| | Total (%) | 100 | 100 | 100 |

Industrial Applicability

The compound of the present invention has an excellent elastase inhibitory activity and is useful for prophylaxis and treatment for various diseases caused by increased elastase activity, such as various diseases by increased protein degradation by elastase, especially respiratory diseases.

The invention claimed is:

1. A heterocyclic compound represented by the following formula (I) or a salt thereof;

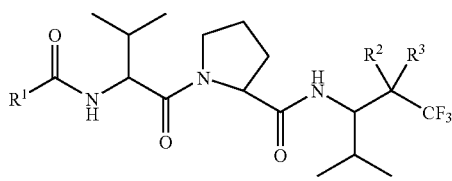

(I)

wherein $R^1$ is a heterocyclic group represented by the formula:

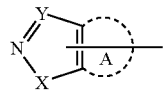

in which A represents the presence or absence of benzene ring, X is oxygen atom, sulfur atom or NH, Y is nitrogen atom or CH, and said heterocyclic group may be substituted by 1 to 3, and the same or different, substituents selected from the group consisting of lower alkyl group; lower alkoxy group; and phenyl group which may be substituted by lower alkyl optionally substituted by a halogen atom, lower alkoxy or a halogen atom; and $R^2$ and $R^3$ are hydrogen atom or hydroxy group, or both may be taken together to form an oxo group, provided that both are not hydrogen atom.

2. A heterocyclic compound represented by the following formula (I-a) or a salt thereof;

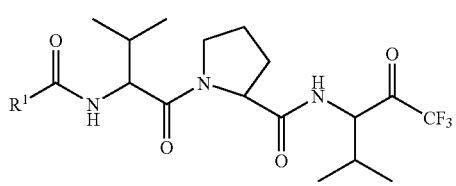

(I-a)

wherein $R^1$ is the same as defined in claim 1.

3. A heterocyclic compound represented by the following formula (I-b) or a salt thereof;

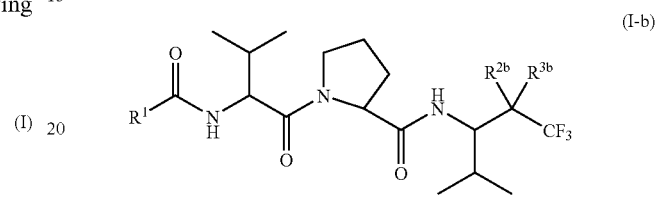

(I-b)

wherein $R^1$ is the same as defined in claim 1, $R^{2b}$ and $R^{3b}$ are hydrogen atom or hydroxy group, provided that both are not hydrogen atom.

4. A heterocyclic compound represented by the following formula (I-c) or a salt thereof;

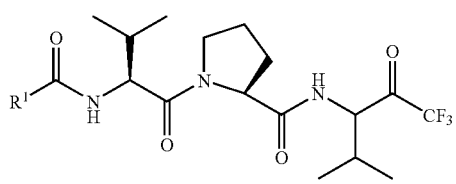

(I-c)

wherein $R^1$ is the same as defined in claim 1.

5. The heterocyclic compound or a salt thereof in accordance to claim 1, wherein the heterocyclic group in $R^1$ represented by the following formula;

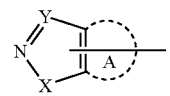

is a group selected from the group consisting of isoxazolyl, isothiazolyl, 1,2,3-thiadiazolyl, benzo[d]isoxazolyl, pyrazolyl, benzotriazolyl, triazolyl, 1H-indazolyl, and benzo[3,4-d]1,2,3-thiadiazolyl, which is optionally substituted.

6. The heterocyclic compound or a salt thereof in accordance to claim 1 wherein the compound is a compound selected from the group consisting of
N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](3,5-dimethylisoxazol-4-yl)carboxamide,
N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl](benzo[d]isoxazol-3-yl)carboxamide,
N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(4-methyl-1,2,3-thiadiazol-5-yl)carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-ethyl-5-methylisoxazol-4-yl)carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methyl-1-phenylpyrazol-4-yl)carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(3-methoxyisoxazol-5-yl)carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[3-(methylethoxy)isoxazol-5-yl]carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5-methylisoxazol-3-yl)carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(5,6-dimethylbenzo[d]isoxazol-3-yl)carboxamide, N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-[1-(4-chlorophenyl)-5-methylpyrazol-4-yl]carboxamide, N-[(1S)-2-((2S)-2-{N-[(1S)-3,3,3-trifluoro-1-(methylethyl)-2-oxopropyl]carbamoyl}pyrrolidinyl)-1-(methylethyl 2-oxoethyl]-[5-methyl-1-(4-methoxyphenyl)pyrazol-4-yl]carboxamide, N-[(1S)-2-((2S)-2-{N-[(1S)-3,3,3-trifluoro-1-(methylethyl)-2-oxopropyl]carbamoyl}pyrrolidinyl)-1-(methylethyl 2-oxoethyl]-[1-(2-fluorophenyl)-5-methylpyrazol-4-yl]carboxamide, and N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-{5-methyl-1-[4-(trifluoromethyl)phenyl]pyrazol-4-yl}carboxamide.

7. A pharmaceutical composition comprising a heterocyclic compound represented by the following formula (I-a) or a pharmaceutically acceptable salt thereof;

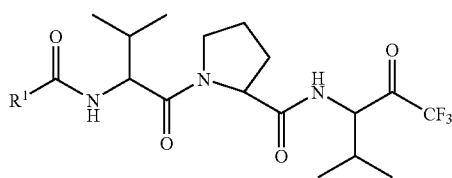

(I-a)

wherein R¹ is the same as defined in claim 1.

8. An elastase inhibitory agent comprising as an active ingredient a heterocyclic compound represented by the following formula (I-a) or a pharmaceutically acceptable salt thereof;

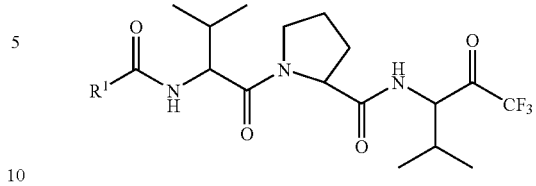

(I-a)

wherein R¹ is the same as defined in claim 1.

9. A method for treating a disease caused by increased elastase activity comprising administering to a patient an effective amount of a heterocyclic compound represented by the following formula (I-a) or a pharmaceutically acceptable salt thereof;

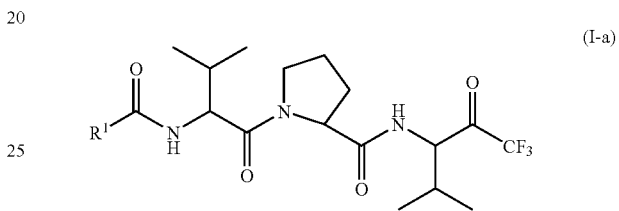

(I-a)

wherein R¹ is the same as defined in claim 1.

10. N-[(1S)-2-((2S)-2-{N-[(1S)-3,3,3-trofluoro-1-(methylethyl)-2-oxopropyl]carbamoyl}pyrrolidinyl)-1-(methylethyl)-2-oxoethyl]-(5-methyl-1-phenylpyrazol-4-yl)carboxamide.

11. N-[(1S)-2-((2S)-2-{N-[(1S)-3,3,3-trifluoro-1-(methylethyl)-2-oxopropyl]carbamoyl}pyrrolidinyl)-1-(methylethyl)-2-oxoethyl]-(1-tert-butyl-5-methylpyrazol-4-yl)carboxamide.

12. The heterocyclic compound or a salt thereof in accordance to claim 2, wherein the heterocyclic group in R¹ represented by the following formula;

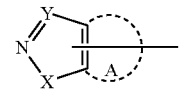

is a group selected from the group consisting of isoxazolyl, isothiazolyl, 1,2,3-thiadiazolyl, benzo[d]isoxazolyl, pyrazolyl, benzotriazolyl, triazolyl, 1H-indazolyl, and benzo[3,4-d]1,2,3-thiadiazolyl, which is optionally substituted.

* * * * *